US008557302B2

(12) United States Patent
Duan et al.

(10) Patent No.: US 8,557,302 B2
(45) Date of Patent: Oct. 15, 2013

(54) ***ANDROGRAPHIS PANICULATA* EXTRACT**

(75) Inventors: Jifeng Duan, Pudong (CN); Zhiming Ma, Suzhou (CN); Xiaoqiang Yan, Nan Hui (CN); Weihan Zhang, Pudong (CN); Tao Wang, Pudong (CN); Yu Cai, Changning (CN)

(73) Assignee: Nutrition Science Partners Limited, Hong Kong (CN)

( * ) Notice: Subject to any disclaimer, the term of this patent is extended or adjusted under 35 U.S.C. 154(b) by 618 days.

(21) Appl. No.: 12/264,646

(22) Filed: Nov. 4, 2008

(65) Prior Publication Data

US 2009/0117210 A1 May 7, 2009

Related U.S. Application Data

(62) Division of application No. 11/934,143, filed on Nov. 2, 2007.

(51) Int. Cl.
*A61K 36/00* (2006.01)

(52) U.S. Cl.
USPC .................................................. 424/725

(58) Field of Classification Search
None
See application file for complete search history.

(56) References Cited

U.S. PATENT DOCUMENTS

| | | | |
|---|---|---|---|
| 6,358,526 B1 | 3/2002 | Mergens et al. | |
| 7,341,748 B2 | 3/2008 | Yan et al. | |
| 7,625,945 B2 | 12/2009 | Yan et al. | |
| RE42,718 E | 9/2011 | Yan et al. | |
| 8,084,495 B2 | 12/2011 | Orozco et al. | |
| RE43,423 E | 5/2012 | Yan et al. | |
| 2002/0068098 A1 | 6/2002 | Babish et al. | |
| 2003/0059434 A1* | 3/2003 | Grupe et al. | 424/184.1 |
| 2003/0059471 A1 | 3/2003 | Compton et al. | |
| 2003/0091517 A1 | 5/2003 | Rojanapanthu et al. | |
| 2003/0101076 A1 | 5/2003 | Zaleski | |
| 2003/0104076 A1* | 6/2003 | Berkulin et al. | 424/725 |
| 2004/0053858 A1 | 3/2004 | Berg | |
| 2004/0151792 A1 | 8/2004 | Tripp et al. | |
| 2005/0215628 A1 | 9/2005 | Yan et al. | |
| 2006/0063831 A1* | 3/2006 | Hancke Orozco et al. | 514/473 |
| 2006/0246156 A1 | 11/2006 | Yan et al. | |
| 2006/0263449 A1* | 11/2006 | Hsu et al. | 424/725 |
| 2007/0202164 A1 | 8/2007 | Wang et al. | |
| 2007/0218114 A1 | 9/2007 | Duggan et al. | |
| 2009/0117209 A1 | 5/2009 | Duan et al. | |
| 2009/0117210 A1 | 5/2009 | Duan et al. | |

FOREIGN PATENT DOCUMENTS

| | | |
|---|---|---|
| CN | 1042077 | 5/1990 |
| CN | 148 837 6 | 4/2004 |
| CN | 1626076 A | 6/2005 |
| CN | 1628764 A | 6/2005 |
| JP | 2000034233 | 2/2000 |
| JP | 2001058969 | 3/2001 |
| JP | 2004-75638 | 3/2004 |
| KR | 1020050067951 A | 7/2005 |
| WO | WO 2005/087223 A1 | 3/2005 |
| WO | WO 2005/104722 A2 | 11/2005 |
| WO | WO 2006/008115 A1 | 1/2006 |
| WO | WO 2007/098686 A1 | 9/2007 |
| WO | WO 2009/059158 A1 | 5/2009 |

OTHER PUBLICATIONS

Rao et al., "Flavonoids and Andrographolides From *Andrographis paniculata*," in Phytochemistry, vol. 65, issue 16, Aug. 2004, Abstract only.
Akbarsha et al., Antifertility effect of *Andrographis paniculata* (pees) in male albino rat, Indian Journal of Experimental Biology, 28:421-426, 1990.
Basak et al., "Implication of the protein convertases furin, PC5 and PC7 in the cleavage of surface glycoproteins of Hong Kong, Ebola and respiratory syncytial viruses: a comparative analysis with fluorogenic peptides", Biochem J., 353:537-45, 2001.
Calabrese et al., A Phase I Trial of Andrographolide in HIV Positive Patients and Normal Volunteers, Phytother. Res. 14:333-338, 2000.
Shen et al., "Andrographolide prevents oxygen radical production by human neutrophils: possible mechanism(s) involve in its anti-inflammatory effect", British Journal of Pharmacology 135:399-406, 2002.
Puri et al., "Immunostimulant Agents from *Andrographis paniculata*", Journal of National Products vol. 56, No. 7, pp. 995-999, 1993.
Trivedi et al.,"Hepatoprotective and antioxidant property of *Andrographis paniculata* (Nees) in BHC induced liver damage in mice" Indian J. Exp. Biol. 39(1):41-6, 2001.
Zhang et al., "Antihyperglycaemic and anti-oxidant properties of *Andrographis paniculata* in normal and diabetic rats" Clinical and Experimental Pharmacology and Physiology, 27:358-363, 2000.
Singha et al., "Antimicrobial activity of *Andrographis paniculata*," Fitoterapia, 74:692-694, 2003.
Townsend et al., "Extracts of Chinese Herbs Inhibit IL-1beta- and UV-induced MMP Expression in Cultured Human Keratinocytes," FASEB Journel, Mar. 2001, vol. 15, No. 4, p. A184.
Habtemariam, Andrographolide Inhibits the Tumor Necrosis Factor-Alpha-Induced Upregulation of ICAM-1 Expression and Endothelial-Monocyte Adhesion.

(Continued)

*Primary Examiner* — Chris R Tate
(74) *Attorney, Agent, or Firm* — Finnegan, Henderson, Farabow, Garrett & Dunner LLP.

(57) ABSTRACT

An extract of *Andrographis paniculata* extract containing andrographolide, 14-deoxyandrographolide, 14-deoxy-11, 12-dehydroandrographolide, neoandrographolide, polysacchorides, and flavanoids. Also disclosed is a pharmaceutical composition containing such an extract and its use for treating inflammatory bowel disease.

2 Claims, No Drawings

(56) References Cited

OTHER PUBLICATIONS

Rajagopal et al., "Andrographolide, a potential cancer therapeutic agent isolated from *Andrographis paniculata*", Journal of Experimental Therapeutics and Oncology, 3(3):147-158, 2003.

Panossian et al., "Effect of andrographolide and Kan Jang—fixed combination of extract SHA-10 and extract SHE-3—on proliferation of human lymphocytes, production of cytokines and immune activation markers in the whole blood cells culture", Phytomedicine, 9(7):598-605, 2002.

See et al., "Increased tumor necrosis factor alpha (TNF-. alpha.) and natural killer cell (NK) function using an integrative approach in late stage cancers", Immunological Investigations, 31(2):137-153, 2002.

Habtemariam, S., "Andrographolide inhibits the tumor necrosis factor-.alpha .-induced upregulation of ICAM-1 expression and endothelial-monocyte adhesion", Phytotherapy Research, 12(1):37-40, 1998.

Kumar et al., "Anticancer and immunomodulatory potential of DRF-3188, an analogue of andrographolide", Novel Compounds from Natural Products in the New Millenium, 205-216, 2004.

Thamaree et al., "The effect of andrographolide on the production of proinflammatory cytokines by in vitro stimulated human blood cells", Inflammation Res., 46, Suppl. 3, S224, 1997.

Achike et al., "Nitric Oxide, Human Diseases and the Herbal Products that Effect the Nitric Oxide Signalling Pathway," Clinical & Experimental Pharmacology & Physiology, 30: 605-615 (2003).

Balmain et al., "Minor Diterpenoid Constituents of *Andrographis paniculata* Nees," J. Chem. Soc. Perkin. Trans. I (1973): 1247-1251.

Burgos et al., "Testicular toxicity assessment of *Andrographis paniculata* dried extract in rats," J. Ethnopharmacol., 58(3): 219-224 (1997).

Chang et al., "Dehydroandrographolide succinic acid monoester as an inhibitor against the human immunodeficiency virus," Proc. Soc. Exp. Biol. Med., 197(1): 59-66 (1991).

Chen et al., "Nine new *ent*-labdane diterpenoids from the aerial parts of *Andrographis paniculata*," Helvetica Chimica Acta, 89:2654-2664 (2006).

Chen et al., "Studies on flavonoids of *Andrographis paniculata*," China J. Chinese Materia Medica., 31(5):391-395 (2006).

Chen et al., "Studies on diterpenoids from *Andrographis paniculata*," China J. Chinese Materia Medica., 31(19):1594-1597 (2006).

Coon et al., "*Andrographis paniculata* in the Treatment of Upper Respiratory Tract Infections: A Systematic Review of Safety and Efficacy," Planta Med., 70(4): 293-298 (2004).

Deng et al., Chinese Pharm. Bull., 17:195-198 (1982).

Fujita et al., "On the diterpenoids of *Andrographis paniculata*: x-ray Crystallographic analysis of andrographolide and structure determination of new minor diterpenoids," Chem. Pharm. Bull., 32(6):2117-2125 (1984).

George et al., "Investigations on plant antibiotics. Part IV. Further search for antibiotic substances in Indian medicinal plants," Indian Journal of Medical Research, (37): 169-181 (2004).

Ghosh et al., "Isolation of *Andrographis paniculata* leaf protein with antifungal property," Acto. Phytopathologica et Entomologica Hungarica, 39(4):377-881(2004).

Gupta et al., "Flavonoids of *Andrographis paniculata*," Phytochemistry, 22(1):314-315 (1983).

Gupta et al., "Antidiarrheal activity of diterpenes of *Andrographis paniculata* (kalmegh) against *Escherichia coli* enterotoxin in in vivo models," International Journal of Crude Drug Research, (28): 273-283 (1990).

Gupta et al., "Antisecretory (antidiarrhoeal) activity of Indian medicinal plants against *Escherichia coli* enterotoxin-induced secretion in rabbit and guinea pig ileal loop models," Inl. J, Pharmacog., 31(3):198-204 (1993).

Gupta et al., "Flavonoid glycoside of *Andrographis paniculata*," Indian J. Chem., 35 B:512-513 (1996).

Habtemariam, "Natural Inhibitors of Tumor Necrosis Factor-α Production, Secretion and Function," Planta Medica, 66:303-313 (2000).

Herbs, *Andrographis paniculata's* wide range of medicinal Powers, (2002).

Jalal et al., "Formation of three new Flavones by differentiating callus cultures of *Andrographis paniculata*," Phytochemistry, 18:149-151 (1979).

Jantan et al., "Ent-14β-Hydroxy-8(17),12-Labdadien-16,15-Olide-3β,19 Oxdide: a Diterpene from the aerial parts of *Andrographis paniculata*," Phytochemistry, 37(5):1477-1479 (1994).

Kakrani et al., "Traditional treatment of gastro-intestinal tract disorders in Kutch district, Gujarat state, India," Journal of Natural Remedies, 2/1: 71-75 (2002).

Kleipool, "Constituents of *Andrographis paniculata* nees," Nature, 169(4288):33-34 (1952).

Madav et al., "Analgesic, antipyretic and antiulcerogenic effects of andrographolide," Indian J. Pharm. Sci., 57(3):121-125 (1995).

Madav et al., "Anti-inflammatory activity of andrographolide," Fitoterapia, 67:452-458, (1996).

Mahadevan et al., "Safety of selective cyclooxygenase-2 inhibitors in inflammatory bowel disease," Am. J. Gastroenterology, 97(4): 910-4 (2002) (Abstract).

Matsuda et al., "Studies on the cell differentiation induces of *Andrographis paniculata*," Tennen Yuki Kagobutsu Toronkai Koen Yoshishu, 33:433-440 (1991) (Abstract).

Matsuda et al., "Cell differentiation-inducing diterpenes from *Andrographis paniculata* Nees," Chem. Pharm. Bull., 42(6):1216-1225 (1994).

Mishra et al., "*Andrographis paniculata* (Kalmegh): A Review," Pharmacognosy Reviews, 1(2):283-298 (2007).

Misra et al., "Antimalarial activity of traditional plants against erythrocytic stages of *Plasmodium berghei*," International Journal of Pharmacognosy, (29): 19-23 (1991).

Nazimudeen et al., "Effect of *Andrographis paniculata* on snake venom-induced death and its mechanism," Indian Journal of Pharmaceutical Sciences, (40):132-133 (1978).

Otake et al., "Screening of Indonesian plant extracts for anti-human immunodeficiency virus type 1 (HIV-1) activity," Phytotherapy Research, (9): 6-10 (1995).

Panossian et al., "Effect of *Andrographis paniculata* extract on progesterone in blood plasma of pregnant rats," Phytomedicine, 6(3):157-161 (1999). (Abstract).

Peng et al., "Modulation of Lianbizi injection (andrographolide) on some immune functions," Zhongguo Zhongyao Zazhi, 27(2):147-150 (2002) (Abstract).

Poolsup et al., "*Andrographis paniculata* in the symptomatic treatment of uncomplicated upper respiratory tract infection: systematic review of randomized controlled trials," J. Clin. Pharm. Ther., 29(1): 37-45 (2004).

Pramanick et al., "Andropanolide and isoandrographolide, minor diterpenoids from *Andrographis paniculata*: structure and X-ray crystallographic analysis," J. Nat. Prod., 69: 403-405 (2006).

Qian et al., "A comparison of pharmacological effects between CXL extract and CXL compound prescription," Journal of Luzhou Medical School, 11(3): 189-191 (1988).

Reddy et al., "A flavone and an unusual 23-carbon terpenoid from *Andrographis paniculata*," Phytochemistry, 62:1271-1275 (2003).

Reddy et al., "A new BIS-Andrographolide ether from *Andrographis paniculata* Nees and evaluation of anti-HIV activity," Natural Product Research, 19(3):223-230 (2005).

Saxena et al., "Phytochemicals from *Andrographis paniculata*," Indian J. Chem., 42B:3159-3163 (2003).

Shen et al., "*ent*-Labdane diterpenoids from *Andrographis paniculata*," J. Nat. Prod., 69:319-322 (2006).

Vedavathy et al., "Antipyretic activity of six indigenous medicinal plants of Tirumala Hills, Andhra Pradesh, India," Journal of Ethnopharmacology, 33(1-2): 193-196 (1991).

Wang et al., "A Discussion on the effect of the extraction process of Chinese traditional medicine on the quality of the resulting drug," Heilongjiang Chinese Medicine, No. 2: 45-46 (1992).

Wang et al., "Andrographolide reduces inflammation-mediated dopaminergic neurodegeneration in mesencephalic neuron-glia cultures by inhibiting microglial activation," Journal of Pharmacology and Experimental Therapeutics, 308(3):915-983 (2004) (Abstract).

(56) References Cited

OTHER PUBLICATIONS

Wang et al., "Chemical constituents from leaves of *Andrographis paniculata*," *J. China Pharma. Univ.*, 36(5):405-407 (2005). Abstract.
Xia, "Andrographolide Attenuates Inflammation by Inhibition of NF-κb Activation Through Covalent Modification of Reduced Cysteine 62 of p50[1]," *The Journal of Immunology*, 4207-4217 (2004).
Yao et al., "Mechanism of inhibition of HIV-1 infection in vitro by a purified extract of *Prunella vulgaris*," *Virology*, 187(1): 56-62 (1992).
Zhang et al., "Effects of 14-Deoxyandrographolide and 14-Deoxy-11, 12-Didehydroandrographolide on Nitric Oxide Production in Cultured Human Endothelial Cells," *Phytotherapy Research*, 13:157-159 (1999).
Zhang et al., "Experimental Studies of the destructive actions of *Andrographis paniculata* nees on endotoxin in vitro,"*Chinese J. of Integrated Traditional and Western Medicine in Intensive and Critical Care*, 7(4):212-214 (2000). Abstract.
Zhang et al., "New Diterpenoids from *Andrographis paniculata* (Burm. f.) nees," *J. of Integrative Plant Biology*, 48(9): 1122-1125 (2006).
Zhong et al., "Three salts of labdanic acids from *Andrographis paniculata* (Acanthaceae)," *Acta Botanica Sinica*, 43:1077-1080 (2001).
Zhou et al., "Two new *ent*-labdane diterpenoid glycosides from the aerial parts of *Andrographis paniculata*," *Journal of Asian Natural Products Research*, 10(10):939-943 (2008).
Andrographis Paniculata Tablets, *The Pharmacopoeia of People's Republic of China* (2000 ed.), vol. I, p. 541 (2000).
Andrographis Paniculata Tablets, *The Pharmacopoeia of People's Republic of China* (2005 ed.), vol. I, pp. 549-550 (2005).
*Guidance for Industry Botanical Drug Products*, U.S. Department of Health and Human Services Food and Drug Administration, Center for Drug Evaluation and Research (CDER), Jun. 2004.
*Practical Techniques for National Qualification Examination of Professional Skills in Chinese medication*, Professional Skills, Shanghai Science and Technology Press, China, p. 164 (2003).
Herba Andrographis, *World Health Organization (WHO) monographs on selected medicinal plants*, vol. 2. pp. 12-24 (2002).
Office Action mailed Jul. 7, 2008, in U.S. Appl. No. 11/934,143.
Amendment in Reply to Non-Final Office Action of Jul. 7, 2008 with Exhibits A & B, filed Nov. 7, 2008, in U.S. Appl. No. 11/934,143.
Final Office Action mailed Mar. 20, 2009, in U.S. Appl. No. 11/934,143.
Amendment and Reply Under 37 C.F.R. § 1.114 filed Sep. 18, 2009, in U.S. Appl. No. 11/934,143.
Office Action mailed Dec. 15, 2009, in U.S. Appl. No. 11/934,143.
Reply to Office Action filed Mar. 15, 2010, in U.S. Appl. No. 11/934,143.
Final Office Action mailed Jun. 16, 2010, in U.S. Appl. No. 11/934,143.
Amendment and Reply under 37 C.F.R. §1.114, filed Dec. 15, 2010, in U.S. Appl. No. 11/934,143.
William J. Sandborn, "Declaration of William J. Sandborn, M.D., under 37 C.F.R. § 1.132" with Exhibit 1, filed on Dec. 15, 2010, in U.S. Appl. No. 11/934,143.
Jianguo Ji, "Declaration under 37 C.F.R. § 1.132" with Exhibits 1-4, filed on Dec. 15, 2010, in U.S. Appl. No. 11/934,143.
Jifeng Duan, "Declaration under 37 C.F.R. § 1.132," filed on Dec. 15, 2010, in U.S. Appl. No. 11/934,143.
Li Wang, "Declaration under 37 C.F.R. § 1.132," filed on Dec. 15, 2010, in U.S. Appl. No. 11/934,143.
Zhiming Ma, "Declaration under 37 C.F.R. § 1.132," filed on Dec. 15, 2010, in U.S. Appl. No. 11/934,143.
Tao Wang, "Declaration under 37 C.F.R. § 1.132," filed on Dec. 15, 2010, in U.S. Appl. No. 11/934,143.
Weihan Zhang, "Declaration under 37 C.F.R. § 1.132," filed on Dec. 15, 2010, in U.S. Appl. No. 11/934,143.
Weihan Zhang, "First Declaration under 37 C.F.R. § 1.132," filed on Dec. 15, 2010, in U.S. Appl. No. 11/934,143.
Weihan Zhang, "Second Declaration under 37 C.F.R. § 1.132," filed on Dec. 15, 2010, in U.S. Appl. No. 11/934,143.
Xiaoqiang Yan, "Declaration under 37 C.F.R. § 1.132," filed on Dec. 15, 2010, in U.S. Appl. No. 11/934,143.
Xun Zhang, "Declaration under 37 C.F.R. § 1.132," filed on Dec. 15, 2010, in U.S. Appl. No. 11/934,143.
Yu Cai, "Declaration under 37 C.F.R. § 1.132," filed on Dec. 15, 2010, in U.S. Appl. No. 11/934,143.
Yuqing Wang, "Declaration under 37 C.F.R. § 1.132," filed on Dec. 15, 2010, in U.S. Appl. No. 11/934,143.
Supplemental Amendment and Reply under 37 C.F.R. §1.114, filed Apr. 6, 2011, in U.S. Appl. No. 11/934,143.
Office Action mailed Aug. 1, 2006, in U.S. Appl. No. 11/116,678.
Amendment in Reply to Action of Aug. 1, 2006 filed Dec. 1, 2006, in U.S. Appl. No. 11/116,678.
Final Office Action mailed Feb. 21, 2007, in U.S. Appl. No. 11/116,678.
Reply to Action of Feb. 21, 2007 with Exhibit A, filed May 21,2007, in U.S. Appl. No. 11/116,678.
Office Action mailed Jun. 2, 2009, in U.S. Appl. No. 11/674,557.
Reply to Office Action filed Oct. 1, 2009, in U.S. Appl. No. 11/674,557.
Final Office Action mailed Jan. 4, 2010, in U.S. Appl. No. 11/674,557.
Reply to Final Office Action filed Apr. 2, 2010, in U.S. Appl. No. 11/674,557.
Advisory Action mailed Apr. 16, 2010, in U.S. Appl. No. 11/674,557.
Office Action mailed Jun. 16, 2010, in U.S. Appl. No. 11/674,557.
PCT Notification of Transmittal of the International Search Report and the Written Opinion of the International Searching Authority, mailed Sep. 13, 2006, in International Application No. PCT/US2005/008317.
PCT Notification of Transmittal of the International Search Report and the Written Opinion of the International Searching Authority, or the Declaration, mailed Jun. 7, 2007, in International Application No. PCT/CN2007/000616.
PCT International Preliminary Report on Patentability issued Sep. 2, 2008, in International Application No. PCT/CN2007/000616.
PCT Notification of Transmittal of the International Search Report and the Written Opinion of the International Searching Authority, or the Declaration, mailed Jan. 26, 2009, in International Application No. PCT/US2008/082022.
PCT Notification of Transmittal of the International Search Report and the Written Opinion of the International Searching Authority, or the Declaration, mailed Dec. 9, 2005, in International Application No. PCT/US05/14288.
PCT International Preliminary Report on Patentability mailed Nov. 9, 2006, in International Application No. PCT/US2005/14288.
Office Action mailed Jun. 23, 2010, in Reissue U.S. Appl. No. 12/717,260.
Reply to Office Action filed Dec. 21, 2010, in Reissue U.S. Appl. No. 12/717,260.
Jianguo Ji, "Declaration under 37 C.F.R. §1.132" with Exhibit 1, dated Dec. 21, 2010, filed on Dec. 21, in Reissue U.S. Appl. No. 12/717,260.
Weihan Zhang, "First Declaration under 37 C.F.R. §1.132," dated Dec. 21, 2010, filed on Dec. 21, in Reissue U.S. Appl. No. 12/717,260.
Weihan Zhang, "Second Declaration under 37 C.F.R. §1.132," dated Dec. 21, 2010, filed on Dec. 21, in Reissue U.S. Appl. No. 12/717,260.
Final Office Action mailed Feb. 9, 2011, in Reissue U.S. Appl. No. 12/717,260.
Response to Final Office Action mailed Mar. 10, 2011, filed Mar. 10, 2011, in Reissue U.S. Appl. No. 12/717,260.
Advisory Action mailed Mar. 25, 2011, in Reissue U.S. Appl. No. 12/717,260.
Supplemental Reply under 37 C.F.R. §1.116, filed Apr. 6, 2011, in Reissue U.S. Appl. No. 12/717,260.
Bao W., "Determination of Dehydroandrographolide in *Andrographis paniculata* Tablets by FIA," Chinese Traditional Patent Medicine, 25(12):976-978 (2003).

(56) References Cited

OTHER PUBLICATIONS

Cai S., et al., "Factors impacting the determination of andrographolide and dehydroandrographolide content in *Andrographis paniculata* tablets," Chinese Traditional Patent Medicine, 27(3):361-362 (2005).

Feng Y., et al., "Determination of deoxyandrographolide content in *Andrographis paniculata* tablets by TLC scanning," Chinese Traditional Patent Medicine, 14(5):17-18 (1992).

Huang P. et al., "Determination of dehydroandrographolide content in *Andrographis paniculata* tablets by HPLC," Journal of Guangxi Traditional Chinese Medical University, 7(3):70-71 (2004).

Jiang Zemin, President of the People's Republic of China, Pharmaceutical Administration Law of the People's Republic of China (2001).

Weihan Zhang, Third Declaration Under 37 C.F.R. § 1.132, dated Mar. 10, 2011.

Hasko et al., Immunology 103: 473-478 (2001).

Assche et al., "Daclizumab, a humanised monoclonal antibody to the interleukin 2 receptor (CD25), for the treatment of moderately to severely active ulcerative colitis: a randomised, double blind, placebo controlled, dose ranging trial," Gut 55;1568-1574 (2006).

Feagan et al., "Omega-3 Free Fatty Acids for theMaintenance of Remission in Crohn Disease," *JAMA*, 299(14):1690-1697 (2008).

Rutgeerts et al., "Onercept for Moderate-to-Severe Crohn's Disease: A Randomized, Double-Blind, Placebo-Controlled Trial," Clinical Gastroenterology and Hepatology, 4:888-893 (2006).

Sandborn et al., "Anti-CD3 antibody visilizumab is not effective in patients with intravenous corticosteroid-refractory ulcerative colitis," *Gut*, 59: 1485-1492 (2010).

Tang et al., "Herbal extract HMPL-004 in Active Ulcerative Colitis: A Randomized Comparison with Sustained Release Mesalamine," American Journal of Gastroenterology (2010).

Pre-IND Submission Meeting Briefing Document (Redacted) (2005).

Slide presented to FDA in Jul. 2010.

Communication pursuant to Rule 114(2) EPC in EP1996165, dated Apr. 29, 2010, enclosing Third Party Observations.

Schwyzer et al., "About Andograholide," Helvetica Chimica Acta, 34 (2): 652-677(1951).

Notebook pages on side-by-side ethanol tests, dated Jul. 25, 2005.

*Ex parte Subramanyam* (BPAI, Mar. 29, 2010).

Chemical Abstracts, 1990, 133(15): 687-688.

Chemical Abstracts, 1982, 97(19): 23.

Office Action mailed May 12, 2011, in U.S. Appl. No. 11/934,143.

Reply to Office Action filed Jul. 21, 2011, in U.S. Appl. No. 11/934,143.

Notice of Allowance and Fee(s) Due mailed Jul. 1, 2011, in Reissue U.S. Appl. No. 12/717,260.

Divisional Reissue U.S. Appl. No. 13/189,444, filed Jul. 22, 2011.

Hancke et al., "A double-blind study with a new monodrug: decrease of symptoms and improvement of recovery from common colds," *Phytotherapy Research*, (9): 559-562 (1995).

Saxena et al., "High-performance thin-layer chromatographic analysis of heptoprotective diterpenoids from *Andrographis paniculata*," *Phytochem Anal*, 11:34-36 (2000).

Zhao et al., "Determination of andrographolide, deoxyandrographolide and neoandrographolide in the Chinese herb *Andrographis paniculata* by micellar electrokinetic capillary chromatography," *Phytochem Anal*, 13: 222-227 (2002).

Communication pursuant to Article 94(3) EPC in EP 1747008, dated Dec. 3, 2009.

Amendment in reply to Communication pursuant to Article 94(3) EPC of Dec. 3, 2009, filed Jun. 3, 2010, in EP 1747008.

Communication pursuant to Article 94(3) EPC in EP 1747008, dated Jul. 5, 2010.

Reply to Communication pursuant to Article 94(3) EPC of Jul. 5, 2010, filed Jan. 14, 2011, in EP 1747008.

Communication pursuant to Article 94(3) EPC in EP 1747008, dated Feb. 24, 2011.

Bhan et al., "Screening and optimization of *Andrographis paniculata* (Burm.f.) Nees for total andrographolide content, yield and its components," *Scientia Horticulturae*, 107: 386-391 (2006).

Melchior et al., "Double-blind, placebo-controlled pilot and phase III study of activity of standardized *Andrographis paniculata* Herba Nees extract fixed combination (Kan jang) in the treatment of uncomplicated upper-respiratory tract infection," *Phytomedicine*, 7(5): 341-350 (2000).

Communication pursuant Article 94(3) EPC in European Patent Application No. 05742174.5, dated Sep. 27, 2011, Examiner Thalmair-De Meyere.

Final Office Action mailed Oct. 18, 2011, in U.S. Appl. No. 11/934,143.

Notice of Appeal under 37 C.F.R. § 41.31 and Appeal Brief Under Board Rule § 41.37, both filed Jan. 18, 2012, in U.S. Appl. No, 11/934,143.

Office Action mailed Jan. 18, 2012, in U.S. Appl. No. 12/969,395.

Supplementary European Search Report issued in European Patent Application No. 08845832.8, dated Mar. 15, 2012.

Sheeja et al., "Antioxidant and anti-inflammatory activities of the plant *Andrographis paniculata* Nees," *Immunopharmacology and Immunotoxicology*, 28: 129-140 (2006).

European Patent Application No. 08845832.8: Response to Extended European Search Report of Mar. 15, 2012, filed Oct. 12, 2012.

European Patent Application No. 05742174.5: Communication pursuant Article 94(3) EPC, dated Apr. 2, 2013.

European Patent Application No. 07711017.9: Communication pursuant to Article 94(3) EPC, dated Apr. 25, 2013.

U.S. Appl. No. 12/969,395: Final Office Action mailed Oct. 12, 2012.

\* cited by examiner

ANDROGRAPHIS PANICULATA EXTRACT

CROSS REFERENCE TO RELATED APPLICATIONS

This application is a divisional application of U.S. Ser. No. 11/934,143, filed Nov. 2, 2007, the content of which is incorporated herein by reference.

BACKGROUND

Inflammatory bowel disease includes chronic gastrointestinal disorders characterized by infiltration of inflammatory cells into the mucosa of the digestive tract. Ulcerative colitis and Crohn's disease are two prevalent conditions among them.

Ulcerative colitis takes place in the large intestine (i.e., colon). The inner lining of the disordered intestine becomes inflamed and develops ulcers.

Crohn's disease most commonly affects the end of the small intestine (i.e., terminal ileum) and parts of the large intestine. It causes inflammation that extends much deeper into the layers of the intestinal wall than ulcerative colitis.

Both ulcerative colitis and Crohn's disease are attributed to dysregulation of pro-inflammatory cytokine, including TNFα and IL-1β. See, e.g., McClane S. J. et al., *Journal of Parenteral and Enteral Nutrition* 23, 1999. Therapeutic agents have been developed based on down-regulation of pro-inflammatory cytokine. For example, 5-aminosalicylic acid, an inhibitor of TNFα signaling events, has been used to treat ulcerative colitis. See, e.g., *Therapeutic Immunology* Ed. Austen, K. F., Blackwell Publishing, 2001, 159-167. However, most inflammatory bowel disease therapeutics have limited efficacy or significant side effects.

There is still a need to develop more effective therapeutic agents for treating inflammatory bowel disease.

SUMMARY

This invention is based on a surprising finding that an extract of *Andrographis paniculata* effectively exerts a curative effect against inflammatory bowel disease. The extract contains andrographolide lactones, polysacchorides, and flavanoids; constituting 10-22% (preferably 13-17%), 18-28% (preferably 20-25%), and 10-15% (preferably 12-14) of the dry weight of the extract, respectively. The andrographolide lactones include andrographolide, 14-deoxyandrographolide, 14-deoxy- 11,12-dehydroandrographolide, and neoandrographolide, which constitute 2-20% (preferably 3-10%, more preferably 6-10%), 0.01-6% (preferably 0.01-2%, more preferably 0.01-1%), 1-6% (preferably 2-5%, more preferably 2-4%), and 1-5% (preferably 2-4%) of the dry weight of the extract, respectively.

Another aspect of this invention relates to a method of treating inflammatory bowel disease (including Crohn's disease and ulcerative colitis). The method includes administering to a subject in need of the treatment an effective amount of the above-described extract.

Also within the scope of this invention are a pharmaceutical composition containing the extract described above and a pharmaceutically acceptable carrier, the use of such a composition to treat inflammatory bowel disease, and the use of such a composition for the manufacture of a medicament for treating this disease.

Details of several embodiments of the invention are set forth in the description below. Other features, objects, and advantages of the invention will be apparent from the description, and also from the claims.

DETAILED DESCRIPTION

To prepare the extract of this invention, one can immerse the aerial part of *Andrographis paniculata* in 80-95% ethanol, collect the ethanol phase, and then remove the ethanol. An actual example is provided below. The extract thus obtained can be further purified by thin layer chromatography, flash column chromatography, high performance liquid chromatography, or any other suitable methods.

This invention includes methods of treating inflammatory bowel disease by administering to a subject in need thereof an effective amount of the extract of this invention. The term "an effective amount" refers to the amount of the extract which is required to confer one of the above-described therapeutic effects in the subject. Effective amounts may vary, as recognized by those skilled in the art, depending on route of administration, excipient usage, and the possibility of co-usage with other agents. Preferably, the effective amount is 1-100 mg/kg/day based on the dry weight of the extract. The term "treating" refers to administering the extract to a subject that has inflammatory bowel disease, or has a symptom of the disease, or has a predisposition toward the disease, with the purpose to cure, heal, alleviate, relieve, alter, remedy, ameliorate, improve, or affect the disease, the symptoms of the disease, or the predisposition toward the disease.

To practice one of the above-described methods, one administers to a subject in need thereof orally, rectally, parenterally, by inhalation spray, or via an implanted reservoir a composition that is either the above-mentioned extract alone or a mixture of the extract and a pharmaceutically acceptable carrier. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. Tablets may also be coated for delivery or cosmetic effects. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A rectal composition can be any rectally acceptable dosage form including, but not limited to, cream, gel, emulsion, suspension, suppository, and tablet. One preferred dosage form is a suppository having a shape and size designed for introduction into the rectal orifice of the human body. A suppository usually softens, melts, or dissolves at body temperature. Suppository excipients include, but are not limited to, theobroma oil (cocoa butter), glycerinated gelatin, hydrogenated vegetable ails, mixtures of polyethylene glycols of various molecular weights, and fatty acid esters of polyethylene glycol.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow #10.

A suitable in vitro assay can be used to preliminarily evaluate the efficacy of the above-described extract in inhibiting expression of TNFα or IL-1β. The extract can further be examined for its efficacy in treating inflammatory bowel disease by in vivo assays. For example, the extract can be administered to an animal (e.g., a mouse model) or human having inflammatory bowel disease and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

EXAMPLE 1

Preparation of the *Andrographis paniculata* Extract

Dry powder of *Andrographis paniculata* leaves (350 kg) was immersed in 90% ethanol (2,100 kg). The mixture was refluxed at 75-80° C. for two hours. The ethanol phase was collected and the solid residue was subjected to extraction again. The ethanol solutions were combined, filtered, and concentrated to afford a wet mixture having a density of 1.00-1.10 g/ml.

A small amount of the mixture was dried and analyzed for its composition by high performance liquid chromatography and spectrophotometry. The result showed that the dry extract contained andrographolide lactones (14.8% of the dry weight of the extract), polysaccharides (24.6%) and flavanoids (12.8%). Among the andrographolide lactones, andrographolide was at 9.2% of the dry weight of the extract, 14-deoxyandrographolide at <0.1%, 14-deoxy-11,12-dehydroandrographolide 2.6%, and neoandrographolide 3.0%. Dextrin was added (0.03 kg) to the wet mixture, which was then spray-dried (inlet: 185-195° C.; outlet: 90-100° C.). The solid extract thus obtained was ground, sieved, and packaged to form tablets and capsules as described below.

Tablets were prepared as follows. Starch (10 g) and sugar (10 g) were mixed with purified water (80.0 g) to yield a paste. Separately, the extract (500.0 g), starch (140.0 g), microcrystalline cellulous (337.5 g), and the paste were mixed, wet granulized, and dried at 55° C. The dried granules (957.6 g) and magnesium stearate (2.4 g) were mixed for 5 minutes. The final mixture was compressed to form tablets (400 mg/tablet, eqv. to 200 mg the extract/tablet). The tablets were film-coated with a paste prepared by mixing hypromellose (7.5 g), propylene glycol (1.6 g), titanium dioxide (3.0 g), Food Drug & Cosmetic color lake (0.4 g), and purified water (87.5 g) to afford the desired *Andrographis paniculata* extract-containing tablets.

Capsules were prepared as follows. The extract (340.0 g), pre-dried starch (221.0 g), silicon dioxide (2.125 g), and microcrystalline cellulous (34.0 g) were mixed. The mixture was filled into #0 hard-shell capsules using a capsule filling board to form the desired *Andrographis paniculata* extract-containing capsules (351.25 mg the mixture/capsule, eqv. to 200 mg the extract/capsule).

EXAMPLE 2

Inhibition of TNFα and IL-1β Expression

Peripheral blood monocytes (PBMC) cells are isolated from fresh blood using Ficoll-Paque Plus (Amersham Bioscience), according to the protocol provided by the manufacturer. The cells are suspended in RPMI 1640 media containing 10% FBS at a concentration of $1 \times 10^5$ cells/ml and seeded in a 96-well plate. Each reaction is carried out in three wells.

10 µl of the extract of *Andrographis paniculata* in DMSO is added into each well (final concentrations: 0.1, 0.3, 1, 3, 10, and 30 µg/ml). Dexamethason (final concentration: 10 µM) is used as positive control. 10 µl of the media is used as a negative control. The plate is incubated at 37° C. under 5% $CO_2$ for 15 minutes. After 10 µl aliquots of 100 µg/ml lipopolysaccharide are added to all wells except for the negative controls, the plate is incubated at 37° C. under 5% $CO_2$ overnight.

The plate is spun at 1000 rpm for 15 minutes and the supernatants are collected. Concentrations of TNFα and IL-1β are measured using the TNFα ELISA (Enzyme Linked Immunosorbent Assay) Kit and IL1-β ELISA Kit (Jingmei Bioengineer Technology).

The inhibition ratio is calculated as follows:

$$\text{Inhibition Ratio } (\%) = \left(1 - \frac{C_{extract} - C_{Control}}{C_{LPS} - C_{Control}}\right) \times 100$$

where $C_{extract}$ is the concentration of TNFα or IL-1β in PBMC cells treated with the extract and LPS, $C_{LPS}$ is the concentration of TNFα or IL-1β in PBMC cells treated with LPS and dexamethason, and $C_{Control}$ is the concentration of TNFα or IL-1β in PBMC cells without being treated with LPS or the extract.

EXAMPLE 3

Treatment of Inflammatory Bowel Disease in Mouse Model

Balb/c male mice (18-24 g, purchased from Chinese Academy of Science animal center) are anaesthetized with 1% pentobarbital sodium at 0.05 mg/10 g. 1.5 mg of 2,4,6-trinitrobenzenesulfonic acid in 50% ethanol is administered slowly to each mouse (except blank control mice) via a catheter to induce inflammatory bowel disease. Blank control mice only receive 0.1 ml of 50% ethanol. The mice are treated with the test sample 24 hours and 2 hours prior to the inflammatory bowel disease administration and daily for 5 days after the administration.

The body weight of each mouse is monitored every day before and after the 2,4,6-trinitrobenzenesulfonic acid administration. The mice are sacrificed 24 hours after the last administration of test samples. Colons are removed and weighed. Furthermore, the colon weight to body weight ratio is calculated and adhesion between colon and other organs is also monitored.

Samples of colon tissues located precisely 2 cm above the anal canal are obtained, fixed in 10% buffered phosphate, embedded in paraffin, sectioned, and stained with hematoxylin/eosin. The degree of inflammation on microscopic cross sections is graded from 0 to 4 (0: no signs of inflammation; 1: a very low level of inflammation; 2: a low level of leukocyte infiltration; 3: a high level of leukocyte infiltration, a high vascular density, and a thickened colon wall; and 4: transmural infiltrations, loss of goblet cells, a high vascular density, and a thickened colon wall).

EXAMPLE 4

Clinical Treatment of Ulcerative Colitis

To study the efficacy of the *Andrographis paniculata* extract in treating ulcerative colitis, a randomized, double-dummy, active controlled 8-week clinical trial was conducted at 5 locations in Shanghai, China in compliance with the International Conference on Harmonisation-Good Clinical Practice (ICH-GCP) guidelines. 120 patients with colonoscopy-confirmed mildly to moderately active ulcerative colitis were assigned to two groups (60 patients/group). One group was treated with the *Andrographis paniculata* extract-containing tablets mentioned above (3 times daily, 2 tablets each time,), and the other was treated with 5-amino-2-hydroxybenzoic acid, i.e., Etiasa (3 times daily, 500-mg granule each time,). All other medications were excluded. The therapeutic effects were assessed biweekly using a scale similar to the partial Mayo Scoring System, and the clinical symptom score reduction (≥50% reduction in symptoms) was calculated. Scores were then retrospectively calculated using the standard partial Mayo scores (PMS), clinical response (improvement ≥2 points or final score of 0) and remission (≤1 PMS score at week 8). Colonoscopies at the beginning and at the end of treatment were rated with a modified Baron score, and biopsies taken during colonoscopy were graded histologically with a scale of 0-3.

Patients in the two groups had similar demographics. In each group, the mean duration of disease ranged from 3.5-3.7 years and the baseline mean PMS was 3.8. In the 53 intent-to-treat patients treated with the extract, the clinical symptom score reduction was 27% in the patients at week 2 and improved to 56% in the patients by week 8. The 55 intent-to-treat Etiasa treated patients showed similar reduction. The clinical response rate at week 8 was 58% in the patients treated with the extract and 58% in the patients treated with Etiasa. The remission rate at week 8 was 43% in the patients treated with the extract and 58% in the patients treated with Etiasa. The results of PMS at the baseline and week 8 in both groups are statistically significant ($p<0.0002$).

Endoscopically, at week 8, 28% of the patients treated with the extract and 24% of those treated with Etiasa were in complete remission (Baron score of 0); and 47% of the patients treated with the extract and 42% of those treated with Etiasa had scores reduced by at least two grades.

Histologically, 19 of the patients treated with the extract and 15 of the patients treated with Etiasa were evaluated. 10 of the 19 patients treated with the extract showed decrease of inflammation scores by 25-50% at week 8, and so did 6 of the 15 patients treated with Etiasa. In the extract-treated group, 12/15 entering with elevated C-reactive protein levels showed normal levels at week 8, compared to 4/6 in the Etiasa-treated group. The results in both groups are statistically significant ($p<0.0001$).

The results indicated that the extract was effective in treating ulcerative colitis. Surprisingly, its efficacy was comparable to or even better than Etiasa.

OTHER EMBODIMENTS

A number of embodiments of the invention have been described. Nevertheless, it will be understood that various modifications may be made without departing from the spirit and scope of the invention. Accordingly, other embodiments are also within the scope of the following claims.

The details of one or more embodiments of the invention are set forth in the accompanying drawings and the description below. Other features, objects, and advantages of the invention will be apparent from the description and drawings, and from the claims.

What is claimed is:
1. A method of treating ulcerative colitis comprising orally administering to a human in recognized need of such treatment an effective amount for treating of a solid dosage form comprising:
   (1) an extract of *Andrographis paniculata* comprising andrographolide lactones:
      wherein said andrographolide lactones comprise:

andrographolide in an amount ranging from 6% to 20% of the dry weight of the extract;

14-deoxyandrographolide in an amount ranging from greater than 0 to less than 1% of the dry weight of the extract;

14-deoxy-11,12-dehydrogen-andrographolide in an amount ranging from 1% to 6% of the dry weight of the extract; and neoandrographolide in an amount ranging from 1% to 5% of the dry weight of the extract, and (2) wherein said solid dosage form for treating ulcerative colitis in a human further comprises at least one pharmaceutically acceptable carrier.

2. The method of claim 1, wherein the extract of *Andrographis paniculata* further comprises polysaccharides and flavonoids.

\* \* \* \* \*